(12) United States Patent
Ziemer et al.

(10) Patent No.: US 6,660,691 B2
(45) Date of Patent: Dec. 9, 2003

(54) HERBICIDAL COMPOSITION COMPRISING BENZOYLPYRAZOLES AND SAFENER (ISOXADIFEN OR MEFENPYR)

(75) Inventors: Frank Ziemer, Kriftel (DE); Andreas van Almsick, Karben (DE); Arnim Köhn, Wiesbaden (DE); Lothar Willms, Hofheim (DE); Hans-Joachim Zeiss, Sulzbach/Ts. (DE); Hermann Bieringer, Eppstein (DE); Erwin Hacker, Hochheim (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 10/164,107

(22) Filed: Jun. 4, 2002

(65) Prior Publication Data

US 2003/0032559 A1 Feb. 13, 2003

(30) Foreign Application Priority Data

Jun. 6, 2001 (DE) ......................... 10 127 328

(51) Int. Cl.[7] .......................... A01N 25/32; A01N 43/80
(52) U.S. Cl. ....................... 504/106; 504/271
(58) Field of Search ................. 504/106, 271, 504/280

(56) References Cited

FOREIGN PATENT DOCUMENTS

| DE | 199 36 520 A1 | 2/2001 |
|----|---------------|--------|
| EP | 1 031 573 A1 | 8/2000 |
| EP | 1 084 618 A1 | 3/2001 |
| WO | WO 99/58509 | 11/1999 |
| WO | WO 99/66795 | 12/1999 |
| WO | WO 01/17353 A1 | 3/2001 |

OTHER PUBLICATIONS

Database WPI AN 1999–313295, also referred to as XP 002215494.

*Primary Examiner*—S. Mark Clardy

(74) *Attorney, Agent, or Firm*—Frommer Lawernce & Haug LLP

(57) ABSTRACT

There are described herbicidal compositions comprising herbicidal compounds of the formula I and a safener-active compound of the formula II or III

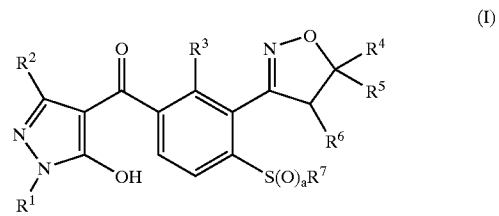

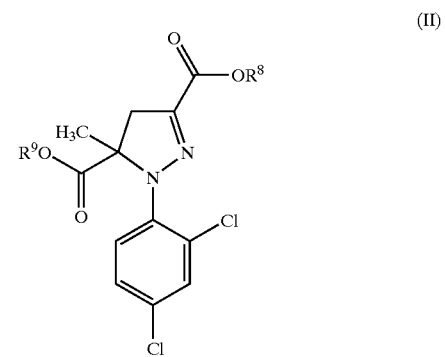

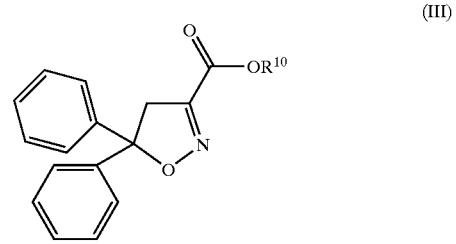

In formulae I, II and III, the symbols $R^1$ to $R^{10}$ are hydrogen, halogen and various organic radicals.

9 Claims, No Drawings

HERBICIDAL COMPOSITION COMPRISING BENZOYLPYRAZOLES AND SAFENER (ISOXADIFEN OR MEFENPYR)

The invention is in the technical field of the crop protection products, in particular herbicide/antidote combinations (active ingredient/safener combinations) which are suitable for use against competing harmful plants in crops of useful plants.

A large number of herbicidal active ingredients are known as inhibitors of the enzyme p-hydroxyphenylpyruvate dioxygenase (HPPD). Only recently, more such active ingredients were disclosed for example in WO 99/58509.

As is the case with many other herbicidal active ingredients, these HPPD inhibitors too are not always sufficiently well tolerated by (i.e. not sufficiently selective in) some important crop plants such as maize, rice or cereals, so that their use is very limited. They can therefore not be employed in some crops, or only at such low application rates that the desired broad herbicidal activity against harmful plants is not ensured. Specifically, many of the above-mentioned herbicides cannot be employed as fully selective herbicides against harmful plants in maize, rice, cereals, sugar cane and some other crops.

To overcome these disadvantages, it is known to employ herbicidal active ingredients in combination with what is known as a safener or antidote. Thus, for example, WO 99/66795 describes various combinations of a large number of HPPD inhibitors with a multiplicity of safeners.

A safener is understood as meaning a compound which compensates for, or reduces, the phytotoxic properties of a herbicide with regard to useful plants, without substantially reducing the herbicidal activity against harmful plants.

Finding a safener for a specific groups of herbicides remains a difficult task since the mechanisms by which a safener reduces the harmful action of herbicides are not known in detail. The fact that a compound in combination with a specific herbicide acts as safener allows therefore no conclusions as to whether such a compound also has a safener action with other groups of herbicides. Thus, it has emerged when safeners were used for protecting the useful plants from herbicide damage that the safeners may still exhibit certain disadvantages in many cases. These include:
  the safener reduces the activity of the herbicide against the harmful plants,
  the useful-plant protecting properties are insufficient,
  the spectrum of the useful plants in which the safener/herbicide is to be employed is not sufficiently wide in combination with a given herbicide,
  a given safener cannot be combined with a sufficiently large number of herbicides.

It was an object of the present invention to provide further combinations of herbicides from the group of the HPPD inhibitors with safeners which are suitable for increasing the selectivity of these herbicides with regard to important crop plants.

There have now been found novel combinations of specific herbicides from the group of the HPPD inhibitors, specifically from the group of the benzoylpyrazoles, which have selected substituents attached in the 3-position of the benzoyl moiety, with some selected safeners which increase the selectivity of these herbicides with regard to important crop plants.

The invention therefore relates to a herbicidally active composition comprising
A) a herbicidally active amount of one or more compounds of the formula (I),

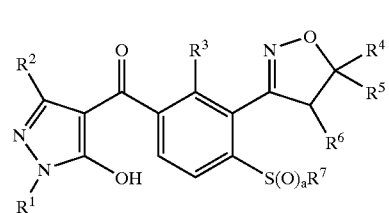

(I)

in which the symbols and indices have the following meanings:
  $R^1$ is $(C_1–C_6)$-alkyl;
  $R^2$ is hydrogen or $(C_1–C_6)$-alkyl;
  $R^3$ is hydrogen, halogen, $(C_1–C_6)$-alkyl, $(C_1–C_6)$-haloalkyl, $(C_1–C_6)$-alkoxy, $(C_1–C_6)$-haloalkoxy, $(C_1–C_6)$-alkylthio, $(C_1–C_6)$-alkylsulfinyl or $(C_1–C_6)$-alkylsulfonyl;
  $R^4$, $R^5$, $R^6$ are hydrogen or $(C_1–C_6)$-alkyl;
  $R^7$ is $(C_1–C_6)$-alkyl;
  a is 0, 1 or 2; and
B) an antidote-effective amount of one or more compounds of the formula (II) or

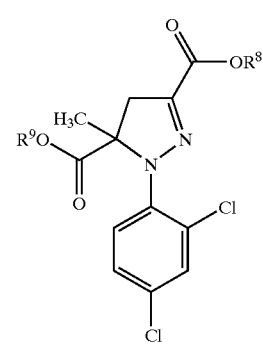

(II)

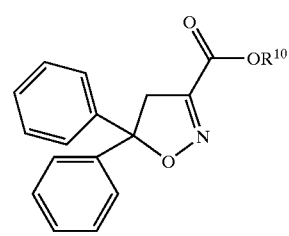

(III)

in which the symbols have the following meanings:
  $R^8$, $R^9$, $R^{10}$ independently of one another are hydrogen or $(C_1–C_4)$-alkyl, including the stereoisomers and the salts conventionally used in agriculture.

Herbicidally active amount for the purposes of the invention refers to an amount of one or more herbicides suitable for having an adverse effect on plant growth.

Antidote-effective amount for the purposes of the invention refers to an amount of one or more safeners suitable for at least partially counteracting the phytotoxic effect of the herbicide or herbicide mixture on a useful plant.

Unless specifically otherwise defined, the definitions given hereinbelow generally apply to the radicals in the formulae of (I) to (III) and the subsequent formulae.

The radicals alkyl, alkoxy, haloalkyl, haloalkoxy and alkylthio and the corresponding unsaturated and/or substituted radicals in the carbon skeleton can be in each case straight-chain or branched. Alkyl radicals, also in the composite meanings such as alkoxy, haloalkyl and the like, preferably have 1 to 4 carbon atoms and are, for example, methyl, ethyl, n- or i-propyl, n-, i-, t- or 2-butyl. "$(C_1-C_4)$-alkyl" is the abbreviation for alkyl having 1 to 4 carbon atoms; the same applies analogously to other general definitions of radicals with bracketed ranges of the possible number of carbon atoms.

Halogen is fluorine, chlorine, bromine or iodine. Haloalkyl is alkyl, alkenyl or alkynyl which is partially or fully substituted by halogen, preferably by fluorine, chlorine, and/or bromine, in particular by fluorine or chlorine, for example $CF_3$, $CHF_2$, $CH_2F$, $CF_2CF_3$, $CH_2FCClFH$, $CCl_3$, $CHCl_2$, $CH_2CH_2Cl$. Haloalkoxy is, for example, $OCF_3$, $OCHF_2$, $OCH_2F$, $OCF_2CF_3$, $OCH_2CF_3$ and $OCH_2CH_2Cl$. The same applies analogously to other halogen-substituted radicals.

Formulae (I) to (III) also encompass all stereoisomers which have the same topological linkage of the atoms, and their mixtures. Such compounds contain one or more asymmetric carbon atoms or else double bonds which are not specified individually in the general formula. The possible stereoisomers which are defined by their specific spatial shape such as enantiomers, diasteriomers, Z- and E-isomers can be obtained from stereoisomer mixtures by customary methods or else be prepared by stereoselective reactions in combination with the use of stereochemically pure starting materials.

Suitable herbicidal active ingredients are in accordance with the invention those compounds of the formula (I) which cannot be employed on their own, or which can not be employed optimally on their own, in crops of useful plants such as cereal crops, rice or maize since they cause too much damage to the crop plants.

Herbicides of the formula (I) are disclosed for example in WO 99/65314 and WO 99/58509.

The publications cited contain detailed information on preparation processes and starting materials. These publications are expressly referred to, they are incorporated into the present application by reference.

The compounds of the formula (II) are known for example from WO 91/07874 and the literature cited therein and can be prepared by, or analogously to, the methods described therein. The compounds of the formula (III) are known from WO 95/07897 and literature cited therein and can be prepared by, or analogously to, the methods described therein.

The publications cited contain detailed information on preparation processes and starting materials. These publications are expressly referred to, they are incorporated into the present application by reference.

For the purposes of the present application, the term "herbicidal compositions" and "herbicide/safener combinations" are to be considered as equal.

Preferred herbicidal compositions are those which comprise compounds of the formula (I), in which the symbols and indices have the following meanings:
$R^1$ is $(C_1-C_6)$-alkyl;
$R^2$ is hydrogen or $(C_1-C_6)$-alkyl;
$R^3$ is halogen or $(C_1-C_6)$-alkyl;
$R^4$, $R^5$, $R^6$ are hydrogen, $(C_1-C_6)$-alkyl;
$R^7$ is $(C_1-C_6)$-alkyl;
a is 0, 1 or 2.

Also preferred are herbicidal compositions comprising safeners of the formula (II) and/or (III), in which $R^8$, $R^9$ and $R^{10}$ independently of one another are hydrogen or $(C_1-C_2)$-alkyl.

Especially preferred are herbicidal compositions comprising compounds of the formula (I), in which $R^3$ is chlorine or methyl.

Also especially preferred are herbicidal compositions comprising compounds of the formula (I) in which a is 2.

The compounds mentioned herein as safeners (antidotes) reduce or compensate for phytotoxic effects which may occur when using the herbicidal active ingredients of the formula (I) in crops of useful plants without essentially adversely affecting the efficacy of the herbicidal active ingredients against harmful plants. Thus, the field of application of conventional crop protection agents can be widened considerably and extended to, for example, crops such as wheat, barley, rice and maize in which the use of the herbicides has previously not been possible or only with limitations, that is to say at low dosages with a narrow spectrum of action.

Herbicidal active ingredients and the safeners mentioned can be applied together (as readymix or by the tank mix method) or sequentially in any desired sequence. The weight ratio of safener to herbicidal active ingredient may vary within wide limits and is preferably in the range of from 1:100 to 100:1, in particular from 1:10 to 10:1. The optimum amount of herbicidal active ingredient and safener depend in each case on the type of the herbicidal active ingredient used or on the safener used and on the nature of the plant stock to be treated and can be determined in each individual case by simple routine preliminary experiments.

Main fields of application for the use of the combinations according to the invention are especially maize and cereal crops such as, for example, wheat, rye, barley, oats, rice, sorghum, but also cotton and soybean, preferably cereals, rice and maize.

Depending on their properties, the safeners employed in accordance with the invention may be used for pretreating the seed of the crop plant (seed dressing) or introduced into the seed furrows prior to sowing or used together with the herbicide before or after emergence of the plants. Pre-emergence treatment includes not only the treatment of the area under cultivation before sowing, but also the treatment of the sown soil which does not yet sustain vegetation. Preferred is the application together with the herbicide. Tank mixes or ready mixes may be employed for this purpose.

The safener application rates required may vary within wide limits, depending on the indication and the herbicidal active ingredient used; they are, as a rule, in the range of from 0.001 to 5 kg, preferably from 0.005 to 0.5 kg, of active ingredient per hectare.

The present invention therefore also relates to a method of protecting crop plants from phytotoxic side effects of herbicides of the formula (I), which comprises applying an antidote-effective amount of a compound of the formula (II) and/or (III) before, after or simultaneously with the herbicidal active ingredient A of the formula (I) to the plants, plant seeds or the area under cultivation.

The herbicide/safener combination according to the invention may also be employed for controlling harmful plants in crops of known genetically modified plants or genetically modified plants yet to be developed. As a rule, the transgenic plants are distinguished by particularly advantageous properties, for example by resistances to certain crop protection agents, resistances to plant diseases or to causative agents of plant diseases such as specific insects or microorganisms such as fungi, bacteria or viruses. Other particular properties concern for example the harvested crop with regard to quantity, quality, storability, composition and specific constituents. Thus, transgenic plants are known with an increased starch content or a modified starch quality, or those with a different fatty acid composition of the harvested crop.

Preferred is the use of the combinations according to the invention in economically important transgenic crops of useful plants and ornamentals, for example of cereals such as wheat, barley, rye, oats, sorghum and millet, rice, cassaya and maize, or else crops of sugar beet, cotton, soybean, oilseed rape, potato, tomato, pea and other vegetables.

When the combinations according to the invention are used in transgenic crops, effects in addition to the effects to be observed against harmful plants in other crops are frequently found, which are specific for application in the particular transgenic crop, for example a modified or specifically widened weed spectrum which can be controlled, modified application rates which may be employed for the application, preferably good combinability with the herbicides to which the transgenic crop is resistant, and an effect on growth and yield of the transgenic crop plants.

The invention thus also relates to the use of the combination according to the invention for controlling harmful plants in transgenic crop plants.

The safeners of the formulae (II) and (III) and their combinations with one or more of the abovementioned herbicidal active ingredients of the formula (I) can be formulated in various ways, depending on the prevailing biological and/or chemico-physical parameters. Suitable possibilities of formulation are, for example, wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil- or water-based dispersions (SC), suspoemulsions, suspension concentrates, dust (DP), oil-miscible solutions (OL), seed-dressing products, granules (GR) in the form of microgranules, spray granules, coated granules and absorption granules, granules for soil application or broadcasting, water-soluble granules (SG), water-dispersible granules (WG), ULV formulations, microcapsules and waxes.

These individual formulation types are known in principle and are described, for example, in: Winnacker-Küchler, "Chemische Technologie" [Chemical engineering], Volume 7, C. Hauser Verlag Munich, 4th Ed., 1986; Wade van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries which may be required, such as inert materials, surfactants, solvents and further additives are likewise known and described, for example, in: "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Based on these formulations, combinations with other crop protectants such as insecticides, acaricides, herbicides, fungicides, and with safeners, fertilizers and/or growth regulators may also be prepared, for example in the form of a readymix or a tank mix.

Wettable powders are preparations which are uniformly dispersible in water and which, besides the active ingredient, additionally comprise ionic and/or nonionic surfactants (wetters, dispersants), for example polyoxethylated alkylphenols, polyoxethylated fatty alcohols, polyoxethylated fatty amides, fatty alcohol polyglycol ether sulfates, alkanesulfonates, alkylbenzenesulfonates, sodium lignosulfonates, sodium 2,2'-dinaphthylmethane-6,6'-disulfonate, sodium dibutylnaphthalene-sulfonate, or else sodium oleoylmethyltaurinate, in addition to a diluent or inert substance. To prepare the wettable powders, the herbicidal active ingredients are ground finely, for example in customary apparatuses such as hammer mills, blower mills and air-jet mills, and simultaneously or subsequently mixed with the formulation auxiliaries.

Emulsifiable concentrates are prepared for example by dissolving the active ingredient in an organic solvent, for example butanol, cyclohexanone, DMF or else high-boiling hydrocarbons such as saturated or unsaturated aliphatic or alicyclic substances, aromatic substances or mixtures of these organic solvents with addition of one or more ionic and/or nonionic surfactants (emulsifiers). The following are examples of emulsifiers which may be used: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as polyoxyethylene sorbitan fatty acid esters. Dusts are obtained in general by grinding the active ingredients with finely divided solid materials, for example talc, natural clays such as kaolin, bentonite and pyrophyllite, or diatomaceous earth.

Suspension concentrates may be water- or oil-based. They can be prepared for example by wet-milling by means of commercially available beat mills, if appropriate with addition of surfactants as, for example, have already been listed above in the case of the other formulation types.

Emulsions, for example oil-in-water emulsions (EW), can be prepared for example by means of stirrers, colloid mills and/or static mixers using aqueous organic solvents and, if appropriate, surfactants as, for example, have already been listed above in the case of the other formulation types.

Granules can be produced either by spraying the active ingredient onto absorptive granulated inert material or by applying active ingredient concentrates to the surface of carriers such as sand, kaolinite or of granulated inert material by means of binders, for example polyvinyl alcohol, sodium polyacrylate or else mineral oils. Suitable active ingredients may also be granulated in the manner which is conventional for the production of fertilizer granules, if desired as a mixture with fertilizers.

As a rule, water-dispersible granules are prepared by the customary method such as spray-drying, fluidized-bed granulation, disk granulation, mixing by means of high-speed mixers, and extrusion without solid inert material.

To prepare disk, fluidized-bed, extruder and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection agents see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise from 0.1 to 99% by weight, in particular from 0.1 to 95% by weight, of active ingredients of the formula (II) and/or (III) or of the herbicide/antidote active ingredient mixture (I) and (II)/(III) and from 1 to 99.9% by weight, in particular from 5 to 99.8% by weight, of a solid or liquid additive and from 0 to 25% by weight, in particular from 0.1 to 25% by weight, of a surfactant.

In wettable powders, the active ingredient concentration is, for example, from approximately 10 to 90% by weight, the remainder to 100% by weight being composed of customary formulation components. In the case of emulsifiable concentrates, the concentration amounts to approximately 1 to 80% by weight. Formulations in the form of dusts comprise from approximately 1 to 20% by weight of active ingredients, sprayable solutions from approximately 0.2 to 20% by weight of active ingredients. In the case of granules such as water-dispersible granules, the active ingredient content depends partly on whether the active compound is in liquid or solid form. As a rule, the active compound content in the water-dispersible granules is between 10 and 90% by weight.

In addition, the active ingredient formulations mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The necessary application rates of the herbicides of the formula (I) varies with the external conditions such as, inter alia, temperature, humidity and the type of the herbicide used. It can be varied within wide limits, for example between 0.001 and 10.0 kg/ha or more of active substance, but it is preferably between 0.005 and kg/ha.

The examples which follow illustrate the invention:

A. FORMULATION EXAMPLES a) A dust is obtained by mixing 10 parts by weight of a compound of the formula (II) and/or (III) or of an active ingredient mixture of a herbicidal active ingredient of the formula (I) and a safener of the formula (II) and/or (III) and 90 parts by weight of talc as inert substance and comminuting the mixture in a hammer mill.

b) A wettable powder with is readily dispersible in water is obtained by mixing 25 parts by weight of a compound of the formula (II) and/or (III) or of an active ingredient mixture of a herbicidal active ingredient of the formula (I) and a safener of the formula (II) and/or (III), 64 parts by weight of kaolin-containing quartz as inert material, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of the formula (II) and/or (III) or of an active ingredient mixture of a herbicidal active ingredient of the formula (I) and a safener of the formula (II) and/or (III), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a bowl mill to a fineness of below 5 microns.

d) An emulsifiable concentrate is obtained from 15 parts by weight of a compound of the formula (II) and/or (III) or of an active ingredient mixture of a herbicidal active ingredient of the formula (I) and a safener of the formula (II) and/or (III), 75 parts by weight of cyclohexanone as solvent and 10 parts by weight of oxethylated nonylphenol as emulsifier.

e) Water-dispersible granules are obtained by mixing

| | |
|---|---|
| 75 parts by weight | of a compound of the formula (II) and/or (III) or of an active ingredient mixture of a herbicidal active ingredient of the formula (I) and a safener of the formula (II) and/or (III), |
| 10 parts by weight | of calcium lignosulfonate, |
| 5 parts by weight | of sodium lauryl sulfate, |
| 3 parts by weight | of polyvinyl alcohol and |
| 7 parts by weight | of kaolin, | grinding the mixture on a pinned-disk mill and granulating the powder in a fluidized bed by spraying on water as granulation liquid.

f) Water-dispersable granules are also obtained by homogenizing and precomminuting

| | |
|---|---|
| 25 parts by weight | of a compound of the formula (II) and/or (III) or of an active ingredient mixture of a herbicidal active ingredient of the formula (I) and a safener of the formula (II) and/or (III), |
| 5 parts by weight | of sodium 2,2'-dinaphthylmethane-6,6'-disulfonate, |
| 2 parts by weight | of sodium oleoylmethyltaurinate, |
| 1 parts by weight | of polyvinyl alcohol, |
| 17 parts by weight | of calcium carbonate and |
| 50 parts by weight | of water | in a colloid mill, subsequently milling the mixture in a beat mill and atomizing and drying the resulting suspension in a spray tower by means of a single-substance nozzle.

B BIOLOGICAL EXAMPLES

In the experiments which follow, compositions according to the invention comprising safeners S1, S2 and herbicides H1 and H2 were employed.

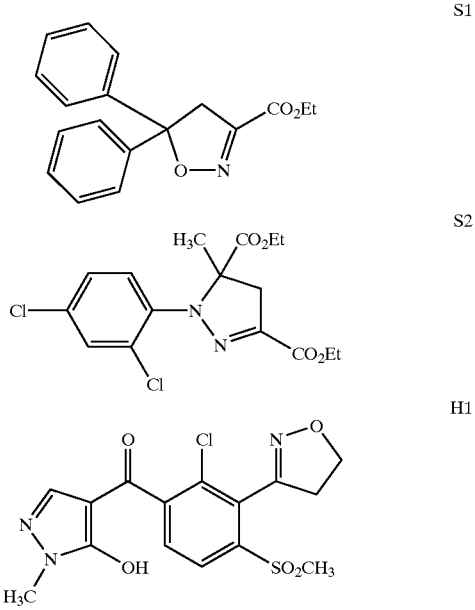

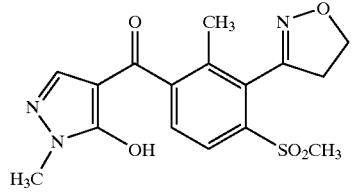

H2

Post-Emergence Experiments:

Seeds of useful plants are placed in soil in the open and covered with soil. At the two-leaf stage, the plants are treated with the herbicides formulated as emulsifiable concentrates or dust and, for comparison purposes, with herbicides and safeners in the form of aqueous dispersions or suspensions or emulsions at an application rate of 300 to 800 l of water per ha (converted) at various dosages. The damage to the useful plants was scored visually 14 or 21 days after the treatment. The results of Examples B1 to B4 demonstrate that the damage in the useful plants was reduced considerably by using the herbicidal compositions comprising herbicide and safener in comparison with using the herbicide only. Depending on the rate of application, the species of the useful plant and the type of the composition according to the invention, the damage is reduced by up to 100% in comparison with using the herbicide. The dosage is shown in grams of active substance per hectare (g a.i/ha).

| Example B1, Reduction of damage in maize, 14 days post-treatment | | |
|---|---|---|
| Dosage [g a.i/ha] Safener S1 | Dosage [g a.i/ha] Herbicide H1 | Damage reduction |
| 50 | 50 | −100% |

| Example B2, Reduction of damage in wheat, 14 days post-treatment | | |
|---|---|---|
| Dosage [g a.i/ha] Safener S2 | Dosage [g a.i/ha] Herbicide H1 | Damage reduction |
| 150 | 150 | −57% |

| Example B3, Reduction of damage in maize, 21 days post-treatment | | |
|---|---|---|
| Dosage [g a.i/ha] Safener S1 | Dosage [g a.i/ha] Herbicide H1 | Damage reduction |
| 150 | 150 | −93% |

| Example B4, Reduction of damage in maize, 21 days post-treatment | | |
|---|---|---|
| Dosage [g a.i/ha] Safener S1 | Dosage [g a.i/ha] Herbicide H2 | Damage reduction |
| 150 | 150 | −92% |

We claim:

1. A herbicidal composition comprising

A) a herbicidally active amount of one or more compounds of the formula (I),

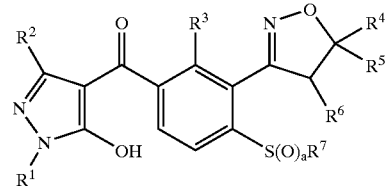

in which the symbols and indices have the following meanings:

$R^1$ is $(C_1-C_6)$-alkyl;
$R^2$ is hydrogen or $(C_1-C_6)$-alkyl;
$R^3$ is hydrogen, halogen, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-alkylsulfinyl or $(C_1-C_6)$-alkylsulfonyl;
$R^4$, $R^5$, $R^6$ are hydrogen or $(C_1-C_6)$-alkyl;
$R^7$ is $(C_1-C_6)$-alkyl;
a is 0, 1 or 2; and B) an antidote-effective amount of one or more compounds of the formula (II) or (III)

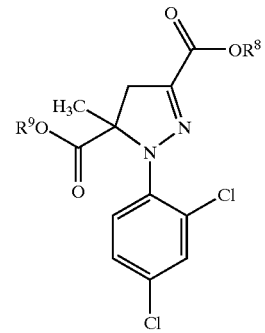

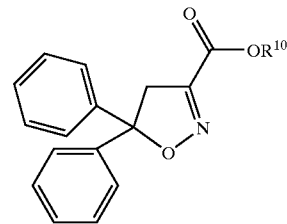

in which $R^8$, $R^9$ and $R^{10}$ independently of one another are hydrogen or $(C_1-C_4)$-alkyl, including the stereoisomers and the salts conventionally used in agriculture.

2. A herbicidal composition as claimed in claim 1, wherein the symbols and indices have the following meanings:

$R^1$ is $(C_1-C_6)$-alkyl;
$R^2$ is hydrogen or $(C_1-C_6)$-alkyl;
$R^3$ is halogen or $(C_1-C_6)$-alkyl;
$R^4$, $R^5$, $R^6$ independently of one another are hydrogen or $(C_1-C_6)$-alkyl;
$R^7$ is $(C_1-C_6)$-alkyl;
a is 0, 1 or 2.

3. A herbicidal composition as claimed in claim 1, wherein $R^8$, $R^9$ and $R^{10}$ in formula II and/or III independently of one another are hydrogen or $(C_1-C_2)$-alkyl.

4. A herbicidal composition as claimed in claim 1, wherein $R^3$ in formula I is chlorine or methyl.

5. A herbicidal composition as claimed in claim 1, wherein a in formula I is 2.

6. A herbicidal composition as claimed in claim 1, wherein the weight ratio herbicide:safener amounts to 1:100 to 100:1.

7. A method of controlling harmful plants in crops, which comprises applying a herbicidally active amount of a herbicide/safener combination as claimed in claim 1 to the harmful plants, plants, plant seeds or the area on which the plants grow.

8. A method as claimed in claim 7, wherein the plants are selected from the group consisting of maize, wheat, rye, barley, oats, rice, sorghum, cotton and soya.

9. A method as claimed in claim 7, wherein the plants are genetically modified.

* * * * *